(12) United States Patent
Hunziker et al.

(10) Patent No.: US 7,615,761 B2
(45) Date of Patent: Nov. 10, 2009

(54) TRACE EVIDENCE DETECTION USING MULTIPLE LASER LIGHT SOURCES

(75) Inventors: Lukas Hunziker, San Jose, CA (US); Georg Herink, Brakel (DE); Arnaud Lepert, Belmont, CA (US)

(73) Assignee: Coherent, Inc., Santa Clara, CA (US)

( * ) Notice: Subject to any disclaimer, the term of this patent is extended or adjusted under 35 U.S.C. 154(b) by 0 days.

(21) Appl. No.: 12/199,984

(22) Filed: Aug. 28, 2008

(65) Prior Publication Data

US 2009/0065710 A1  Mar. 12, 2009

Related U.S. Application Data

(60) Provisional application No. 60/993,185, filed on Sep. 10, 2007.

(51) Int. Cl.
*G01N 21/64* (2006.01)
(52) U.S. Cl. .................................. 250/459.1
(58) Field of Classification Search .......... 250/458.1, 250/459.1
See application file for complete search history.

(56) References Cited

U.S. PATENT DOCUMENTS

| 4,794,260 | A | 12/1988 | Asano et al. | 250/458.1 |
| 5,072,338 | A * | 12/1991 | Hug et al. | 362/553 |
| 5,491,343 | A | 2/1996 | Brooker | 250/458.1 |
| 6,276,798 | B1 | 8/2001 | Gil et al. | 351/205 |
| 6,485,981 | B1 | 11/2002 | Fernandez | 436/71 |
| 7,283,230 | B2 * | 10/2007 | Ostler et al. | 356/317 |
| 7,431,467 | B2 * | 10/2008 | Nath et al. | 362/20 |
| 2003/0005303 | A1 | 1/2003 | Auslander et al. | 713/176 |
| 2005/0282292 | A1 | 12/2005 | Torre-Bueno | 436/180 |
| 2006/0133643 | A1 * | 6/2006 | Bennett et al. | 382/100 |
| 2007/0083124 | A1 | 4/2007 | Ehben et al. | 600/476 |

FOREIGN PATENT DOCUMENTS

EP  1 316 794 A1  6/2003
EP  1 582 860 A1  10/2005

OTHER PUBLICATIONS

U.S. Appl. No. 11/788,291, entitled "Laser Forensic Detection Method and Apparatus," filed Apr. 19, 2007, by David Clark et al., 11 pages in length.
2006 Product Brief entitled "Eclipse Ambient Light Rejection Camera," by Pixim Digital Pixel System (Pixim, Inc.), 2 pages in length.
Book entitled *Fingerprint Detection With Lasers*, by E. Roland Menzel, Chapter 4.3.1 entitled "Filter Placement," and Chapter 5.8 entitled "Night Vision Goggles," copyright 1999, 9 pages in length.
S. Marshall et al., "Locating Semen on Live Skin Using Visible Fluorescence," located on-line at the web site entitled http://www.bvda.com/EN/prdctinf/semen_fluo.html, Apr. 2001 (*Rofin Australia Pty. Ltd.*, Melbourne, Australia), 8 pages in length.
M. Stoilovic, "Detection of Semen and Blood Stains Using Polilight as a Light Source," *Forensic Science International*, vol. 51, Oct. 1, 1991, pp. 289-296.

* cited by examiner

*Primary Examiner*—David P Porta
*Assistant Examiner*—Marcus H Taningco
(74) *Attorney, Agent, or Firm*—Morrison & Foerster LLP

(57) ABSTRACT

A method for detecting trace evidence materials on a surface comprises irradiating the surface with radiation from two or more lasers emitting radiation at different wavelengths selected to stimulate luminescence in the trace materials. The evidence is detected by observing the surface through an optical filter arranged to transmit the luminescence, while blocking transmission of the laser radiation wavelengths reflected or scattered from the surface.

13 Claims, 2 Drawing Sheets

TRACE EVIDENCE DETECTION USING MULTIPLE LASER LIGHT SOURCES

PRIORITY CLAIM

This application claims priority of U.S. Provisional Application No. 60/993,185, filed Sep. 10, 2007, the complete disclosure of which is hereby incorporated by reference.

TECHNICAL FIELD OF THE INVENTION

The present invention relates in general to trace evidence detection using optical radiation stimulated luminescence. The invention relates in particular to stimulating the luminescence using radiation at a plurality of different wavelengths.

DISCUSSION OF BACKGROUND ART

Laser radiation is increasingly being used in crime scene investigation for detecting trace evidence such as fingerprints or bodily fluid residue. Generally a surface being investigated for such trace evidence is irradiated by laser radiation having a wavelength that is absorbed by trace material being sought and will stimulate fluorescence or luminescence characteristic of the material. The laser-radiation-irradiated surface is observed, usually in a darkened environment, through an optical filter that blocks the stimulating radiation and transmits the stimulated luminescence such that trace evidence present on the irradiated surface appears bright against a dark background. The surface may be treated with a dye that can be preferentially absorbed by certain kinds of trace materials and has a brighter luminescence than the material. This is preferred in particular for fingerprint detection.

In a practical apparatus the wavelength of the laser radiation is selected to be able to stimulate fluorescence in a range of trace materials. One disadvantage of this is that not all materials in the range may be equally detectable. Another disadvantage is that, fingerprint detection aside, it may not be clear what trace materials are being detected.

There is a need to increase that range of materials simultaneously detectable by laser stimulated fluorescence. It would be advantageous to be able to identify in situ trace materials that are detected.

SUMMARY OF THE INVENTION

The present invention is directed to a method of detecting trace evidence materials on a surface. In one aspect the inventive method comprises irradiating the surface with radiation from at least first and second lasers. The first and second lasers emit radiation at respectively first and second wavelengths selected to stimulate luminescence in one or more of the trace materials. The irradiated surface is observed through an optical filter arranged to transmit the luminescence, and essentially block transmission of the laser radiation wavelengths.

The terminology "essentially block" as used in connection with the above-recited optical filter recognizes that such a filter can usually not be made completely opaque to the laser radiation wavelengths. Such a filter can normally, however, be expected to block about 99% or more of the laser radiation wavelengths while transmitting more than about 90% of the luminescence.

The surface may be simultaneously or repeatedly sequentially irradiated by the first and second wavelength laser radiations. In an embodiment of the inventive method in which the surface is repeatedly sequentially irradiated by the first and second wavelength laser radiations, the first and second wavelengths are characteristic absorption wavelengths of a particular trace evidence material being detected. The particular material has respectively first and second absorption coefficients at the first and second wavelengths. The power of the first and second wavelength radiations is adjusted corresponding to the first and second wavelengths such that the luminescence stimulated by each of the first and second wavelength is equally bright. Accordingly if the particular material is present on the surface it will appear to an observer as being a spot of constant brightness, whereas traces of other materials will appear to scintillate at the repetition period of the sequentially delivered radiations.

Alternatively the first and second wavelength radiations may be selected to stimulate luminescence in respectively first and second ranges of materials with at least one material in the first range of materials not being included in the second range of materials. It should be noted here that the term "luminescence" as used in this description and the appended claims should be interpreted as including fluorescence.

DETAILED DESCRIPTION OF THE INVENTION

Figure 1:
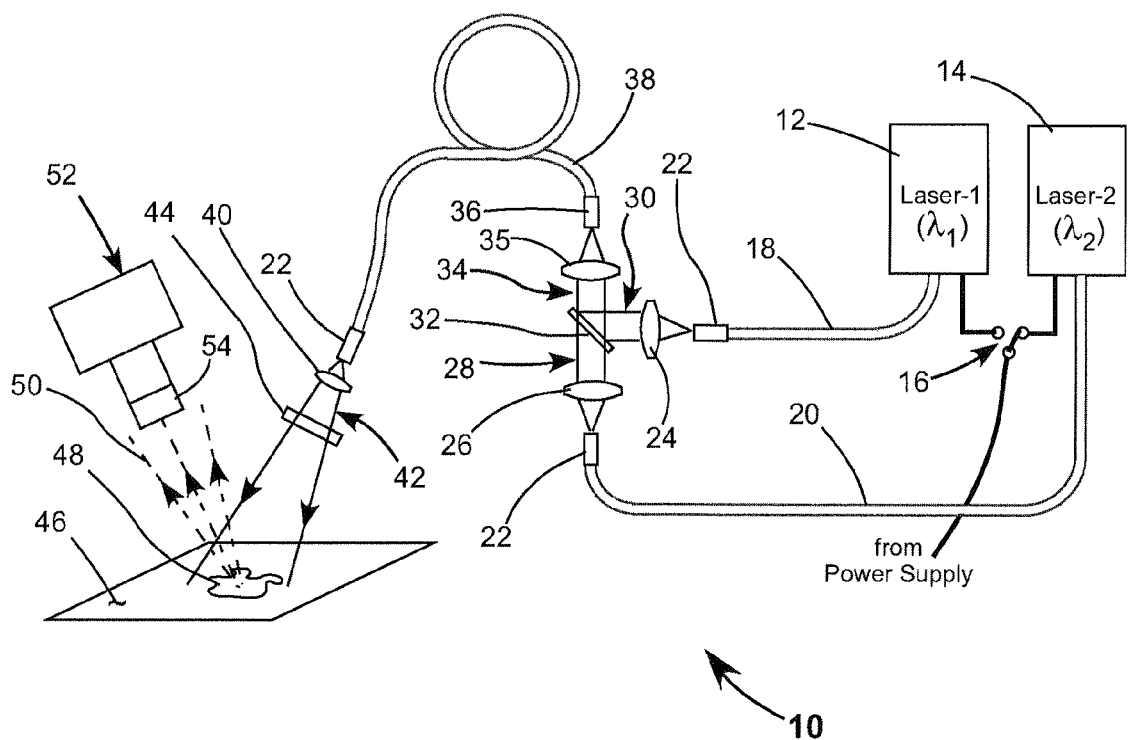
FIG. 1 schematically illustrates a preferred embodiment including first and second lasers emitting radiation at respectively first and second wavelengths, an optical arrangement for combining radiation from the lasers into a single beam, an optical arrangement for irradiating a surface to be examined with radiation from the single beam, a camera for recording any luminescence emitted from the surface responsive to the irradiation, and an optical filter located between the surface and the camera for preventing radiation having the first and second wavelengths from reaching the camera.

Referring now to the drawings, wherein like features are designated by like reference numerals, FIG. 1 schematically illustrates a preferred embodiment 10 of trace evidence detection apparatus in accordance with the present invention. Apparatus 10 includes first and second lasers 12 and 14, respectively. Lasers 12 and 14 emit laser radiation at wavelengths $\lambda_1$ and $\lambda_2$, respectively. The output power of the lasers is selectively variable. Lasers 12 and 14 are powered by current from a power supply not shown. Power is directed alternatively to one or the other laser by a switch 16.

Radiation from lasers 12 and 14 is delivered via optical fibers (or optical fiber bundles) 18 and 20, respectively. Each fiber (bundle) is terminated by a ferrule 22 from which the radiation is delivered from the fiber. A positive lens 24 collimates radiation from fiber 18 into a collimated beam 30. A positive lens 26 collimates radiation from fiber 20 into a collimated beam 28. Beams 28 and 30 are combined by a dichroic beamsplitter 32 into a single beam-path 34. Whichever of beam 28 or 30 is propagating on path 34, that beam is focused by a positive lens 35 and a ferrule 36 into a transport fiber (or fiber bundle) 18. Radiation from fiber 38 exits the fiber via a ferrule 22 and is formed by a lens 40 into a relatively narrowly diverging beam 42. Beam 42 is transmitted through a diffuser 44 to a surface 46 to be examined for trace evidence. In a preferred mode of operation of the apparatus, described in detail further hereinbelow, lasers 12 and 14 are switched periodically on and off, with one laser on while the other is off, surface 46 is irradiated in sequence by wavelengths $\lambda_1$ and $\lambda_2$.

Certain spots or stains on the surface, such as spot 48, emit fluorescence radiation 50 in response to the irradiation by beam 42. This fluorescence radiation is detected a video camera 52. The camera is equipped with a filter 54 configured to block whichever of the wavelengths $\lambda_1$ and $\lambda_2$ that is instantly in beam 42, while transmitting as much other radiation as possible in a range of wavelengths to which camera 52 is responsive. Preferably, a separate, narrow blocking-band is provided for each wavelength, thereby allowing some radiation having wavelengths therebetween to be transmitted. This is particularly advantageous where the irradiating (excitation) wavelengths are within a range of fluorescence wavelengths stimulated by the excitation wavelengths.

Figure 2:
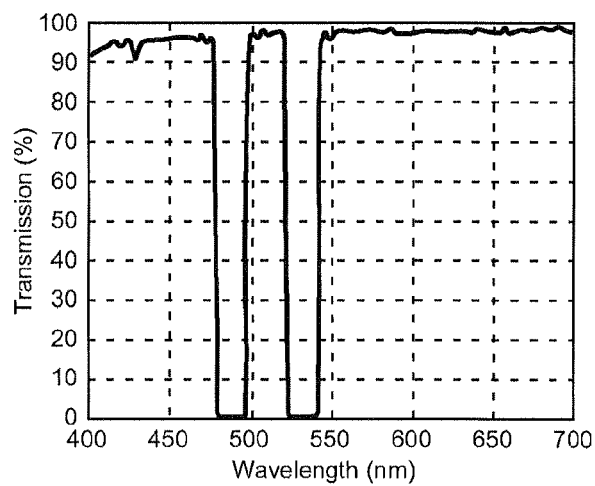
FIG. 2 is a graph schematically illustrating measured transmission as a function of wavelength for one example of the filter of FIG. 1.

FIG. 2 is a graph schematically illustrating transmission versus wavelength for one example of a filter usable with emission wavelengths $\lambda_1$ and $\lambda_2$, of 460 nm and 530 nm. This filter was obtained as part number NF01-488/532/532 from SEMROCK Corporation of Rochester, N.Y.

Figure 3:
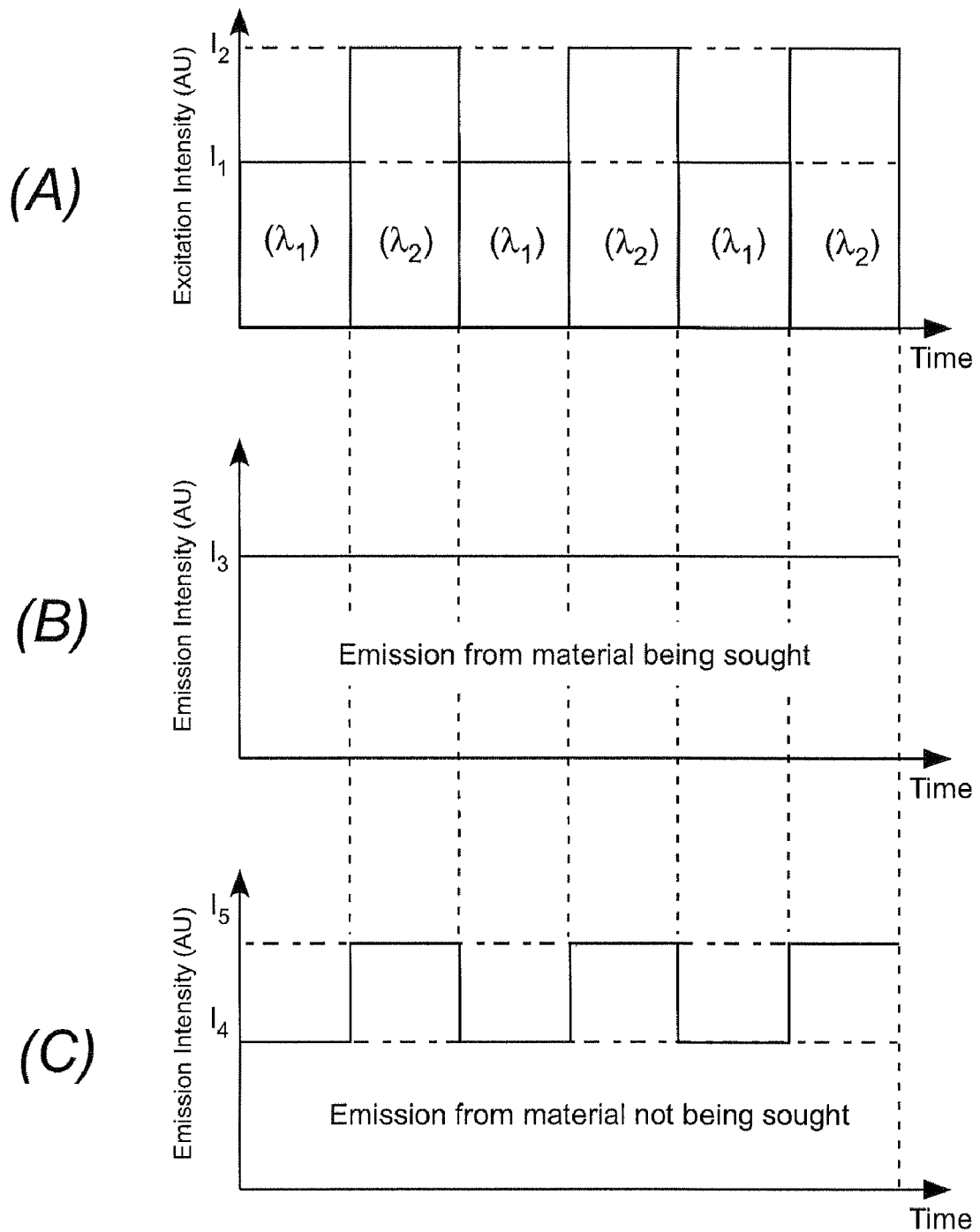
FIG. 3 is a timing diagram schematically illustrating a preferred mode of operation of the apparatus of FIG. 1

FIG. 3 is a timing diagram schematically illustrating a preferred method of operation of apparatus 10. Line (A) schematically illustrates excitation intensity in beam 42 as a function of time as lasers 12 and 14 are switched on and off in sequence thereby irradiating surface 46 with wavelengths $\lambda_1$ and $\lambda_2$ in sequence. Radiation having a wavelength $\lambda_1$ has intensity $I_1$, and radiation having a wavelength $\lambda_2$ has intensity $I_2$. Intensities $I_1$ and $I_2$ are selected by selectively varying the output power of corresponding lasers 12 and 14. The intensities are selected such that each produce about the same emission intensity for a particular trace evidence material being sought, depicted as intensity $I_3$ in line (B) of FIG. 3. A spot of sought material will appear in to camera 54 as a spot of constant glow in a recorded image.

The chance that any other material has the same emission response characteristics as the material being sought is infinitesimally small. Accordingly any such other material will produce a different emission intensity for each of the irradiating (exciting) wavelengths. This is depicted in line (C) of FIG. 3 wherein intensity varies periodically between intensities $I_4$ and $I_5$ in response to sequential irradiation by wavelengths $\lambda_1$ and $\lambda_2$. A spot of material not being sought will appear in camera 54 to flicker in an image recorded thereby.

Those skilled in the art will recognize from the description provided above that the switching period from irradiating with one wavelength to irradiating with another wavelength must be at least equal to and preferably somewhat greater than the response time of the human eye to changes in intensity. If this were not the case, the eye would integrate any flashing spot such that the spot appeared to glow constantly. One suitable irradiation period has been found to be about one-quarter of a second. Were apparatus 10 provided with a means of selectively varying the irradiation-period-per-wavelength, a suitable period could easily be experimentally determined. Those skilled in the art will also recognize that, whatever switching method is used for periodically changing irradiation wavelengths, there should not be any eye-detectable period between sequential irradiations when neither laser is on, or any eye-detectable overlap period when both lasers are otherwise all material on surface 46 would appear to flicker, to some extent, in an image thereof.

It should be noted, here, that while in the timing diagram of FIG. 3, lasers 12 and 14 are indicated as being operated in a CW mode during an "on" period, either of the lasers may be operated in a pulsed mode during an "on" period. Clearly, however, the pulse repetition period must be sufficiently short that the pulsed operation would not be detectable as flickering of an image.

In an experimental evaluation of apparatus 10, lasers 12 and 14 were TracER/OPSL-532™ and TracER/OPSL-460™ lasers, respectively, both available from Coherent Inc, of Santa Clara, Calif. These lasers emit radiation at wavelengths 532 nm and 460 nm respectively. Both lasers are external-cavity, surface-emitting, optically pumped, semiconductor lasers (OPS-lasers) with intra-cavity frequency doubling. Filter 54 was as exemplified above with reference to FIG. 2.

A test surface, on paper, was furnished with traces of cream-soap, skin-cream, sun-blocker, hair-gel, rinsing agent, grease-remover, seminal fluid and saliva. The power of 460 nm-radiation output by laser 12 was about 0.55 Watts (W). The power of 532 nm-radiation output by laser 14 was about 0.83 W. The wavelengths and powers were selected to target seminal fluid, specifically. In recordings made in color by only irradiating with one of each of the two wavelengths it was observed that the seminal fluid spots emitted a different color for each irradiating wavelength. With the camera set for black-and-white (monochrome) operation, the seminal fluid traces appeared to glow constantly in an image, while traces of the other materials appeared to flicker.

Another method of operation of the inventive apparatus is to operate the camera to record and subtract luminescence images taken when the sample is sequentially excited at each of the two wavelengths and form an image from the recorded subtractions. This technique can be used to subtract unwanted background luminescence, thereby improving signal-to-noise ratio of the luminescence image that is generated by the trace evidence of interest. Image processing electronics for performing such image subtraction are not explicitly show in FIG. 1 but can be included in camera 54.

By way of example, many of the dyes used for fingerprint detection have relatively narrow absorption spectra compared to typical substrate materials. If $\lambda_1$ is selected to be resonant with (near an absorption peak of) a particular dye, and the $\lambda_2$ is just off-resonance, subtracting the two images from one another will cancel the background luminescence of the substrate (since the substrate will have the same intensity when excited at each wavelength) but preserve the trace evidence luminescence (since the luminescence generated with wavelength $\lambda_2$ is zero). Recording images using background-subtraction techniques in laser-illuminated trace-evidence detection is described in detail in U.S. patent application Ser. No. 11/788,291, assigned to the assignee of the present invention, and the complete disclosure of which is hereby incorporated by reference.

It should be noted, here, that while lasers 12 and 14 are depicted as separate lasers powered by a common power supply, this should not be construed as limiting the present invention. The lasers may be components of a common package with a common power supply included or may be powered by separate supplies that can be modulated, with modulation interleaved to provide the sequential irradiation. The free-space beam-path combining arrangement of lenses 24, and 26 and beamsplitter 32 may be included in such a package. Further, if individual fibers are used for transporting laser output the free-space combiner may be replaced by an arrangement in which the individual fibers are coupled to a single transport fiber by a wavelength division multiplex (WDM) coupler. It is also possible to use free space optics to combine laser output paths directly from resonators thereof before focusing radiation in the combined path into a fiber.

These and other such modifications may be made to apparatus 10 without departing from the spirit and scope of the present invention.

In summary, the present invention is described above in terms of a preferred and other embodiments. The invention, however, is not limited to the embodiments described and depicted. Rather, the invention is limited only by the claims appended hereto.

What is claimed is:

1. A method for detecting trace evidence materials on a surface, comprising the steps of:
    irradiating the surface with radiation from at least first and second lasers the first and second lasers emitting radiation at respectively first and second wavelengths selected to stimulate luminescence in the trace evidence materials, and the first and second wavelength radiations being delivered repeatedly and sequentially to the surface,
    wherein the first and second wavelengths are characteristic absorption wavelengths of a particular trace evidence material being detected;
    adjusting the power of the first and second wavelength radiations such that the brightness of the luminescence from the particular trace evidence material stimulated by each of the first and second wavelength radiations is substantially similar; and
    observing the surface through an optical filter arranged to transmit the luminescence, and essentially block transmission of the first and second laser radiation wavelengths.

2. The method of claim 1, wherein the luminescence stimulated by each of the first and second wavelength radiations is observed in monochrome.

3. The method of claim 1, wherein the particular trace evidence material is seminal fluid and the first and second wavelengths are respectively about 532 nm and about 460 nm.

4. A method for detecting trace evidence materials on a surface, comprising the steps of:
    irradiating the surface with radiation from at least first and second lasers the first and second lasers emitting radiation at respectively first and second wavelengths selected to stimulate luminescence in the trace evidence materials, and the first and second wavelength radiations being delivered repeatedly and sequentially to the surface; and
    observing the surface through an optical filter arranged to transmit the luminescence, and essentially block transmission of the first and second laser radiation wavelengths,
    wherein the filter transmits luminescence at wavelengths between the first and second wavelengths.

5. A method for detecting trace evidence materials on a surface, comprising the steps of:
    irradiating the surface with radiation from at least first and second lasers the first and second lasers emitting radiation at respectively first and second wavelengths selected to stimulate luminescence in the trace evidence materials, and the first and second wavelength radiations being delivered repeatedly and sequentially to the surface,
    wherein the illumination periods are selected to be longer than the response time at which the human eye perceives intensity changes; and
    observing the surface through an optical filter arranged to transmit the luminescence, and essentially block transmission of the first and second laser radiation wavelengths.

6. A method for detecting trace evidence materials on a surface, comprising the steps of:
    irradiating the surface with radiation from at least first and second lasers the first and second lasers emitting radiation at respectively first and second wavelengths selected to stimulate luminescence in the trace materials,
    wherein the surface is repeatedly sequentially irradiated by the first and second wavelength laser radiations, and
    wherein the first and second wavelengths are characteristic absorption wavelengths of a particular trace evidence material being detected, the particular trace evidence materials having first and second absorption coefficients at respectively the first and second wavelengths;
    adjusting the power of the first and second wavelength radiations corresponding to the first and second absorption coefficients such that the brightness of the luminescence from the particular trace evidence material stimulated by each of the first and second wavelength radiations is substantially similar; and
    observing the surface through an optical filter arranged to transmit the luminescence, and essentially block transmission of the laser radiation wavelengths.

7. The method of claim 6, wherein the illumination periods are selected to be longer than the response time at which the human eye perceives intensity changes.

8. The method of claim 7, wherein the luminescence stimulated by each of the first and second wavelength radiations is observed in monochrome.

9. The method of claim 6, wherein the first wavelength is selected to stimulate luminescence in a first range of materials and the second wavelength is selected to stimulate luminescence in a second range of materials with one or more of the materials in the second range of materials not being included in the first range of materials.

10. An apparatus for detecting trace material on a surface comprising:
    a first laser generating a first beam having a first wavelength;
    a second laser generating a second beam having a second wavelength different from the first wavelength, with the intensity of both said beams being adjustable to elicit a substantially similar level of luminescence in a selected trace material of interest;
    optics for combining the beams along a common path towards the surface;
    a camera for detecting and displaying the luminescence response; and
    means for sequentially and repeatedly activating the first and second lasers with the illumination periods being selected so that the selected trace material will appear substantially flicker free in the display while other trace materials will appear to flicker in the display.

11. An apparatus as recited in claim 10, wherein the first and second wavelengths are both in the visible spectrum.

12. An apparatus as recited in claim 10, further including an optical filter positioned in front of the camera for blocking radiation emitted in the wavelength ranges of the first and second lasers.

13. An apparatus as recited in claim 12, wherein said optical filter transmits luminescence at wavelength between the first and second wavelengths.

* * * * *